United States Patent
Ward et al.

(10) Patent No.: US 8,114,023 B2
(45) Date of Patent: Feb. 14, 2012

(54) ANALYTE SENSING AND RESPONSE SYSTEM

(75) Inventors: W. Kenneth Ward, Portland, OR (US); Michael D. Wood, Portland, OR (US); Heather M. Duman, Portland, OR (US); Bala Nair, Auburn, WA (US)

(73) Assignee: Legacy Emanuel Hospital & Health Center, Portland, OR (US)

( * ) Notice: Subject to any disclaimer, the term of this patent is extended or adjusted under 35 U.S.C. 154(b) by 1412 days.

(21) Appl. No.: 11/592,034

(22) Filed: Nov. 1, 2006

(65) Prior Publication Data

US 2008/0027301 A1    Jan. 31, 2008

Related U.S. Application Data (60) Provisional application No. 60/834,279, filed on Jul. 28, 2006.

(51) Int. Cl.
*A61B 5/00* (2006.01)
*A61B 5/05* (2006.01)

(52) U.S. Cl. .................... 600/365; 600/300; 600/347

(58) Field of Classification Search .................. 600/347, 600/355
See application file for complete search history.

(56) References Cited

U.S. PATENT DOCUMENTS

| | | |
|---|---|---|
| 4,245,634 A | 1/1981 | Albisser et al. |
| 4,431,004 A | 2/1984 | Bessman |
| 4,515,584 A | 5/1985 | Abe |
| 4,822,337 A | 4/1989 | Newhouse |
| 5,062,841 A | 11/1991 | Siegel |
| 5,109,866 A | 5/1992 | Guegan |
| 5,569,186 A | 10/1996 | Lord |
| 5,702,444 A | 12/1997 | Struthers |
| 5,711,861 A | 1/1998 | Ward et al. |
| 5,820,622 A | 10/1998 | Gross |
| 5,885,616 A | 3/1999 | Hsiao et al. |
| 5,995,860 A | 11/1999 | Sun |
| 6,049,727 A | 4/2000 | Crothall |
| 6,056,734 A | 5/2000 | Jacobsen |
| 6,122,535 A | 9/2000 | Kaestle et al. |
| 6,233,471 B1 | 5/2001 | Berner et al. |
| 6,442,413 B1 | 8/2002 | Silver |
| 6,463,321 B2 | 10/2002 | Granger |
| 6,485,437 B1 | 11/2002 | Tapper |
| 6,544,212 B2 | 4/2003 | Galley |
| 6,558,351 B1 | 5/2003 | Steil |
| 6,565,509 B1 | 5/2003 | Say |
| 6,740,072 B2 | 5/2004 | Starkweather |
| 2001/0020137 A1 | 9/2001 | Granger |
| 2002/0120186 A1 | 8/2002 | Keimel |
| 2003/0130616 A1* | 7/2003 | Steil et al. ...................... 604/66 |
| 2005/0027181 A1 | 2/2005 | Goode, Jr. et al. |

(Continued)

OTHER PUBLICATIONS

Gopakumaran et al. "A Novel Insulin Delivery Algorithm in Rats with Type 1 Diabetes: The Fading Memory Proportional-Derivative Method" Artificial Organs. 2005. 29(8): 599-607.*

(Continued)

*Primary Examiner* — Patricia Mallari
(74) *Attorney, Agent, or Firm* — Kolisch Hartwell, P.C.

(57) ABSTRACT

Electrochemical systems for measuring an analyte concentration, and correcting any surplus or deficiency in the measured concentration. More specifically, systems for measuring an analyte level in a fluid with an implantable sensor, processing the measurements with an algorithm, and determining an appropriate fluid infusion rate in response to the measurements.

9 Claims, 7 Drawing Sheets

U.S. PATENT DOCUMENTS

2005/0192557 A1* 9/2005 Brauker et al. ............... 604/503

OTHER PUBLICATIONS

Pfeiffer, EF, Thum, C and Clemens, AH. *The artificial beta cell—a continuous control of blood sugar by external regulation of insulin infusion (glucose controlled insulin infusion system)*. Horm Metab Res 1974, 6: 339-342.

Clemens, AH. *Control algorithms for artificial beta cell*. Horm Metab Res Suppl 1979: 35-38.

Clemens, AH. *Feedback control dynamics for glucose controlled insulin infusion system*. Med Prog Technol 1979, 6: 91-98.

Clemens, AH, Hough, DL and D'Orazio, PA. *Development of the Biostator Glucose clamping algorithm*. Clin Chem 1982, 28: 1899-1904.

Mayfield, RK, Sullivan, FM, Colwell, JA, and Wohltmann, HJ. *Predicting insulin requirements for a portable insulin pump using the Biostator. Evidence for reversible insulin resistance in poorly controlled type I diabetics*. Diabetes 1983, 32: 908-914.

Verdonk, CA, Rizza, RA, Westland, RE, Nelson, RL, Gerich, JE, and Service, FJ. *Glucose clamping using the Biostator GCIIS*. Horm Metab Res 1980, 12: 133-135.

Broekhuyse, HM, Nelson, JD, Zinman, B, and Albisser, AM. *Comparison of algorithms for the closed-loop control of blood glucose using the artificial beta cell*. IEEE Trans Biomed Eng 1981, 28: 678-687.

Cobelli, C and Ruggeri, A. *Evaluation of portal/peripheral route and of algorithms for insulin delivery in the closed-loop control of glucose in diabetes—a modeling study*. IEEE Trans Biomed Eng 1983, 30: 93-103.

Fischer, U, Detschew, W, Jutzi, E, Albrecht, G, Abel, P, Salzsieder, E, Freyse, EJ, Frenzel, S, and Lemke, K. *In vivo comparison of different algorithms for the artificial beta-cell*. Artif Organs 1985, 9: 173-179.

Goriya, Y, Kawamori, R, Shichiri, M, and Abe, H. *The development of an artificial beta cell system and its validation in depancreatized dogs: the physiological restoration of blood glucose homeostasis*. Med Prog Technol 1979, 6: 99-108.

Sekigami, T, Shimoda, S, Nishida, K, Matsuo, Y, Ichimori, S, Ichinose, K, Shichiri, M, Sakakida, M, and Araki, E. *Comparison between closed-loop portal and peripheral venous insulin delivery systems for an artificial endocrine pancreas*. J Artif Organs 2004, 7: 91-100.

Shimoda, S, Nishida, K, Sakakida, M, Konno, Y, Ichinose, K, Uehara, M, Nowak, T, and Shichiri, M. *Closed-loop subcutaneous insulin infusion algorithm with a short-acting insulin analog for long-term clinical application of a wearable artificial endocrine pancreas*. Front Med Biol Eng 1997, 8: 197-211.

Shichiri, M, Kawamori, R, Hakui, N, Yamasaki, Y, and Abe, H. *Closed-loop glycemic control with a wearable artificial endocrine pancreas. Variations in daily insulin requirements to glycemic response*. Diabetes 1984, 33: 1200-1202.

Rebrin, K, Fischer, U, von Woedtke, T, Abel, P, and Brunstein, E. *Automated feedback control of subcutaneous glucose concentration in diabetic dogs*. Diabetologia 1989, 32: 573-576.

Reboldi, GP, Home, PD, Calabrese, G, Fabietti, PG, Brunetti, P, and Massi Benedetti, M. *Time delay compensation for closed-loop insulin delivery systems: a simulation study*. Int J Artif Organs 1991, 14: 350-358.

Albisser, AM, Leibel, BS, Ewart, TG, Davidovac, Z, Botz, CK, and Zingg, W. *An artificial endocrine pancreas*. Diabetes 1974, 23: 389-396.

Kraegen, EW, Campbell, LV, Chia, YO, Meier, H, and Lazarus, L. *Control of blood glucose in diabetics using an artificial pancreas*. Aust N Z J Med 1977, 7: 280-286.

Marliss, EB, Murray, FT, Stokes, EF, Zinman, B, Nakhooda, AF, Denoga, A, Leibel, BS, and Albisser, AM. *Normalization of glycemia in diabetics during meals with insulin and glucagon delivery by the artificial pancreas*. Diabetes 1977, 26: 663-672.

Kadish, AH. *Automation Control of Blood Sugar. I. A Servomechanism for Glucose Monitoring and Control*. Am J Med Electron 1964, 39: 82-86.

El-Shal, SM and El-Rabaie, NM. *A control algorithm for the two-dimensional glucoregulatory system*. Int. J. Systems Sci. 1995, 26: 499-513.

Steil, GM, Panteleon, AE and Rebrin, K. *Closed-loop insulin delivery-the path to physiological glucose control*. Adv Drug Deliv Rev 2004, 56: 125-144.

Bequette, BW. *A critical assessment of algorithms and challenges in the development of a closed-loop artificial pancreas*. Diabetes Technol Ther 2005, 7: 28-47.

Chee, F, Fernando, T and van Heerden, PV. *Closed-loop glucose control in critically ill patients using continuous glucose monitoring system (CGMS) in real time*. IEEE Trans Inf Technol Biomed 2003, 7: 43-53.

Abramovitch, D. *Some Crisp Thoughts on Fuzzy Logic*. in *American Controls Conference*. 1994. Baltimore, MD.

Jaremko, J and Rorstad, O. *Advances toward the implantable artificial pancreas for treatment of diabetes*. Diabetes Care 1998, 21: 444-450.

Kienitz, KH and Yoneyama, T. *A robust controller for insulin pumps based on H-infinity theory*. IEEE Trans Biomed Eng 1993, 40: 1133-1137.

Rollins, L, *Robust Control Theory*, in *18-849b Dependable Embedded Systems*. 1999.

Parker, RS, Doyle, FJ, 3rd and Peppas, NA. *A model-based algorithm for blood glucose control in type I diabetic patients*. IEEE Trans Biomed Eng 1999, 46: 148-157.

Pagurek, B, Riordon, JS and Mahmoud, S. *Adaptive control of the human glucose-regulatory system*. Med Biol Eng 1972, 10: 752-761.

Knobbe, EJ and Buckingham, B. *The extended Kalman filter for continuous glucose monitoring*. Diabetes Technol Ther 2005, 7: 15-27.

Zisser, H, Jovanovic, L, Doyle, F, 3rd, Ospina, P, and Owens, C. *Run-to-run control of meal-related insulin dosing*. Diabetes Technol Ther 2005, 7: 48-57.

Candas, B and Radziuk, J. *An adaptive plasma glucose controller based on a nonlinear insulin/glucose model*. IEEE Trans Biomed Eng 1994, 41: 116-124.

Kan, S, Onodera, H, Furutani, E, Aung, T, Araki, M, Nishimura, H, Maetani, S, and Imamura, M. *Novel control system for blood glucose using a model predictive method*. Asaio J 2000, 46: 657-662.

Hovorka, R, Canonico, V, Chassin, LJ, Haueter, U, Massi-Benedetti, M, Orsini Federici, M, Pieber, TR, Schaller, HC, Schaupp, L, Vering, T, and Wilinska, ME. *Nonlinear model predictive control of glucose concentration in subjects with type 1 diabetes*. Physiol Meas 2004, 25: 905-920.

Hovorka, R, Chassin, LJ, Wilinska, ME, Canonico, V, Akwi, JA, Federici, MO, Massi-Benedetti, M, Hutzli, I, Zaugg, C, Kaufmann, H, Both, M, Vering, T, Schaller, HC, Schaupp, L, Bodenlenz, M, and Pieber, TR. *Closing the loop: the adicol experience*. Diabetes Technol Ther 2004, 6: 307-318.

Trajanoski, Z, Regittnig, W and Wach, P. *Simulation studies on neural predictive control of glucose using the subcutaneous route*. Comput Methods Programs Biomed 1998, 56: 133-139.

Trajanoski, Z and Wach, P. *Neural predictive controller for insulin delivery using the subcutaneous route*. IEEE Trans Biomed Eng 1998, 45: 1122-1134.

Bequette, B. *Practical Approaches to Nonlinear Control: A Review of Process Applications*. Nonlinear Model-based Process Control, NATO ASI Series, Ser. E 1998, 353: 3-32 R. Berber and C. Kravaris (eds.), Kluwer, Dordrecht.

Steil, GM, Rebrin, K, Janowski, R, Darwin, C, and Saad, MF. *Modeling beta-cell insulin secretion—implications for closed-loop glucose homeostasis*. Diabetes Technol Ther 2003, 5: 953-964.

Nomura, M, Shichiri, M, Kawamori, R, Yamasaki, Y, Iwama, N, and Abe, H. *A mathematical insulin-secretion model and its validation in isolated rat pancreatic islets perifusion*. Comput Biomed Res 1984, 17: 570-579.

Ward, WK, Bolgiano, DC, McKnight, B, Halter, JB, and Porte, D, Jr.. *Diminished B cell secretory capacity in patients with noninsulin-dependent diabetes mellitus*. J Clin Invest 1984, 74: 1318-1328.

Hosker, JP, Rudenski, AA, Burnett, MA, Matthews, DR, and Turner, RC. *Similar reduction of first- and second-phase B-cell responses at*

*three different glucose levels in type II diabetes and the effect of gliclazide therapy.* Metabolism 1989, 38: 767-772.

Laury, MC, Takao, F, Bailbe, D, Penicaud, L, Portha, B, Picon, L, and Ktorza, A. *Differential effects of prolonged hyperglycemia on in vivo and in vitro insulin secretion in rats.* Endocrinology 1991, 128: 2526-2533.

Levenston, ME, Beaupre, GS, Jacobs, CR, and Carter, DR. *The role of loading memory in bone adaptation simulations.* Bone 1994, 15: 177-186.

Federiuk, IF, Casey, HM, Quinn, MJ, Wood, MD, and Ward, WK. *Induction of type-1 diabetes mellitus in laboratory rats by use of alloxan: route of administration, pitfalls, and insulin treatment.* Comp Med 2004, 54: 252-257.

Hu, Wen-Jing, Eaton, John W., Ugarova, Tatiana P., and Tang, Liping. *Molecular basis of biomaterial-mediated foreign body reactions.* Blood, Aug. 15, 2001, vol. 98, No. 4, pp. 1231-1238.

Katou, Fuminori, Ohtani, Haruo, Nagura, Hiroshi and Motegi, Katsutoshi. *Procollagen-Positive Fibroblasts Predominantly Express Fibrogenic Growth Factors and Their Receptors in Human Encapsulation Process Against Foreign Body.* J. Pathol. 186:201-208 (1998).

Khouw, Ilse M.S.L., van Wachem, Pauline B., Plantinga, Josee A., Vujaskovic, Zeljko, Wissink, Marcel J.B., de Leij, Lou F.M.H. and van Luyn, Marja J.A. *TGF-β and bFGF affect the differentiation of proliferating procine fibroblasts into myofibrolasts in vitro.* Biomaterials 20 (1999) 1815-1822.

Roberts, Anita B., Piek, Ester, Bottinger, Erwin P., Ashcroft, Gillian, Mitchell, James B., and Flanders, Kathleen C. *Is Smad3 a Major Player in Signal Transduction Pathways Leading to Fibrogenesis?* Thomas L. Petty 43$^{rd}$ Annual Aspen Lung Conference: Mechanisms of Pulmonary Fibrosis, Chest/120/1/July, 2001 Supplement, pp. 43S-47S.

Updike, Stuart J., Shults, Mark C., Gilligan, Barbara J. and Rhodes, Rathbun K. *A Subcutaneous Glucose Sensor With Improved Longevity, Dynamic Range, and Stability of Calibration.* Diabetes Care, vol. 23, No. 2, Feb. 2000, pp. 208-214.

Rousseeuw, Peter J. *Handbook of Statistical Methods for Engineers and Scientists—Robust Estimation and Identifying Outliers*, Chapter 16, pp. 16.1-16.24. Free University Brussels, Belgium. Copyright 1990.

Wolf, Gunter, Ziyadeh, Fuad N., Zahner, Gunther, and Stahl, Rolf A.K., *Angiostensin II-stimulated expression of transforming growth factor beta in renal proximal tubuluar cells: Attenuation after stable transfection with the c-mas oncogene.* Kidney International, vol. 48 (1993), pp. 1818-1827.

* cited by examiner

| FMPD algorithm ||
|---|---|
| Initial BG (mg/dl) | Final BG (mg/dl) |
| 214 | 116 |
| 257 | 115 |
| 346 | 125 |
| 429 | 119 |
| 403 | 118 |
| 355 | 111 |
| Mean 334 | 118 |
| SEM 34 | 2 |

ANALYTE SENSING AND RESPONSE SYSTEM

CROSS REFERENCE TO RELATED APPLICATION

This application claims priority under 35 U.S.C. §119(e) and all applicable international law to U.S. Provisional Patent Application Ser. No. 60/834,279 filed Jul. 28, 2006, which is incorporated herein by reference in its entirety for all purposes.

FIELD OF THE INVENTION

The invention generally relates to electrochemical systems for measuring an analyte concentration and correcting any surplus or deficiency in the measured concentration. More specifically, the invention relates to systems for measuring an analyte level in a fluid with an implantable sensor, processing the measurements with an algorithm, and determining an appropriate fluid infusion rate in response to the measurements.

BACKGROUND

Maintaining appropriate analyte levels in the bloodstream of mammals, including humans, is extremely important, and failure to do so can lead to serious health problems and even death. For example, in diabetic patients, malfunction of the pancreas can lead to uncontrolled blood glucose levels, possibly resulting in hypoglycemic or hyperglycemic shock. To compensate for this and to maintain an appropriate blood glucose level, diabetics must receive timely and correct doses of insulin. Similarly, many other analytes commonly are measured in the blood of humans and in other fluids, for the purpose of determining an appropriate response to any measured surplus or deficiency of the analyte.

One method of measuring an analyte concentration in the blood of a mammal is to use an implantable sensor to measure the concentration, and a number of previous patented inventions relate to various aspects of such sensors. U.S. Pat. No. 5,711,861 to Ward et al. claims a disc-shaped sensor device having multiple anode/cathode pairs of electrodes for taking redundant analyte measurements. U.S. Pat. No. 6,212,416 to Ward et al. adds a coating to the sensor to inhibit formation of collagen or to enhance the sensitivity of the sensor in the presence of the analyte, and claims multiple redundant sensors (as opposed to a single sensor with multiple electrode pairs). U.S. Pat. No. 6,466,810 to Ward et al. claims a sensor with a single cathode and a plurality of anodes on each side, to provide redundant measurements without requiring multiple cathodes.

Once analyte measurements have been obtained with a sensor—whether the sensor is implantable or otherwise—a response often must be determined, typically in the form of a fluid infusion rate to alter the analyte concentration to a more desirable level. The infused fluid may contain the analyte itself, or it may contain a substance the presence of which affects the analyte level. For example, if the measured analyte is glucose, the infused fluid may contain glucose, or it may contain insulin.

Typically, an algorithm is used to determine a fluid infusion rate from analyte measurements, and several such algorithms are known. For example, a glucose-controlled insulin infusion system incorporating a proportional derivative (PD) method is disclosed in U.S. Pat. No. 4,151,845 to Clemens. U.S. Pat. No. 6,558,351 to Steil et al. claims an insulin infusion system using a proportional integral derivative (PID) algorithm that takes a patient's history of glucose levels into account when determining the infusion rate, by integrating the difference between the measured glucose level and the desired glucose level from some prior time up to the present. U.S. Pat. No. 6,740,072 to Starkweather et al. adjusts the parameters of the insulin infusion algorithm dynamically in response to exercise, sleep, and other external events.

However, despite the use of various algorithms to determine a response to a measured analyte concentration, no algorithm has been developed that takes into account both current and prior analyte levels in a manner that adequately reflects the dynamic nature of the measured concentration. In the case of glucose measurements and insulin infusion, for example, none of the previously developed algorithms are able to simulate completely the normal insulin response of a healthy pancreas. Thus, a need exists for an improved system for measuring an analyte concentration, processing the measurements using an algorithm that adequately takes into account the dynamics of the analyte, and determining a response.

DESCRIPTION

The present disclosure generally relates to systems for measuring an analyte level in a fluid with an implantable sensor, processing the measurements with an algorithm, and determining an appropriate fluid infusion rate in response to the measurements. The disclosed sensors generally are suitable for implantation into a mammal, and may include various features such as multiple anode/cathode pairs of electrodes for taking redundant glucose measurements, coatings to inhibit formation of collagen or to enhance the sensitivity of the sensor in the presence of glucose, and/or a single cathode with a plurality of anodes on each side, to provide redundant signals without requiring multiple cathodes. The disclosed algorithms use current and previous analyte values, and current and previous analyte rates of change, to determine an appropriate fluid infusion rate in response. These algorithms weigh more recent analyte values and analyte rates of change more heavily than more remote values and rates of change. This disclosure refers to an algorithm having these characteristics as a "Fading Memory Proportional Derivative" (FMPD) algorithm.

I. IMPLANTABLE SENSORS AND ANALYTE MONITORING SYSTEMS

This section describes a particular embodiment of an analyte sensor suitable for use with the present invention, and a commensurate monitoring system embodiment suitable for use with the disclosed sensor.

Figure 1:
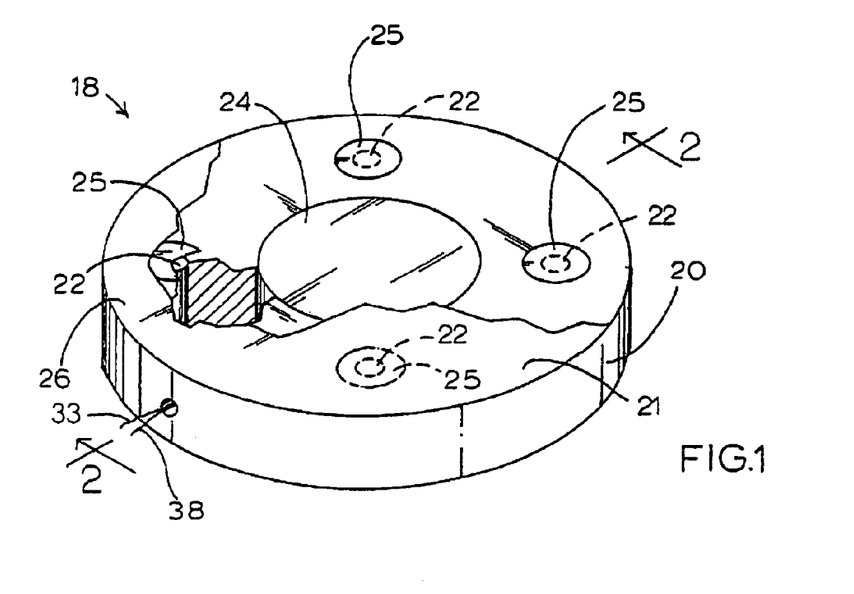
FIG. 1 is a partially cut-away perspective view of an analyte sensor.
Figure 2:
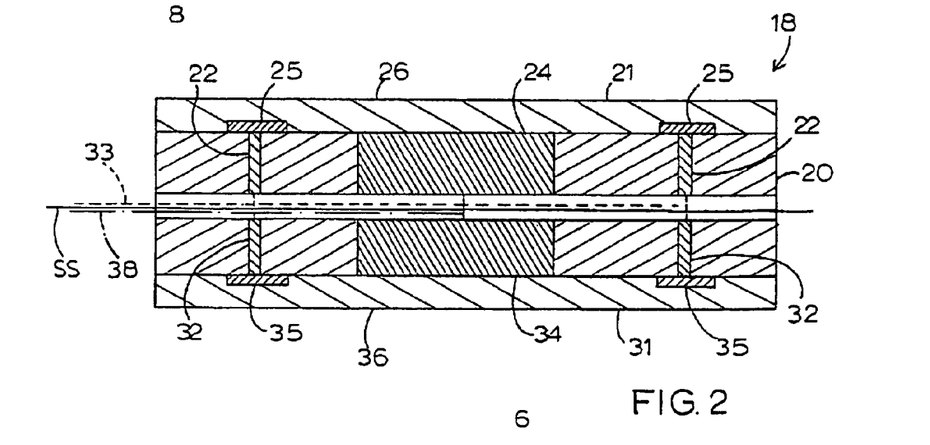
FIG. 2 is a cross-sectional view of the sensor shown in FIG. 1.

FIGS. 1 and 2 illustrate a disc-shaped glucose sensor having two opposing faces, each of which has an identical electrode configuration. Alternatively, a disc-shaped sensor may be used in which an electrode configuration is provided on only one side of the sensor. One of the faces can be seen in the partially cut-away perspective view in FIG. 1. Sensor 18 includes a disc-shaped body 20. On planar face 21 of sensor 18, four platinum anodes 22 are symmetrically arranged around a centrally disposed silver chloride cathode 24. Each anode 22 is covered by an enzyme layer 25 including the active enzyme glucose oxidase and stabilizing compounds such as glutaraldehyde and bovine serum albumin (BSA). A semi-permeable membrane layer 26 covers all of the electrodes and individual enzyme layers. The thickness and porosity of membrane layer 26 is carefully controlled so as to limit diffusion and/or transport of the analyte of interest (in this embodiment, glucose) from the surrounding fluid into the anode sensing regions. The mechanism of selective transport of the analyte of interest through the membrane may involve one or more of the following principles: molecular size exclusion, simple mass transfer, surface tension phenomena, or chemically mediated processes.

FIG. 2 shows a cross-section of sensor 18. Sensor 18 has a plane of symmetry SS, which is normal to the plane of the figure. Under face 31 of sensor 18, anodes 32 are spaced equidistantly apart from cathode 34. Enzyme layers 35 cover anodes 32. A semi-permeable polyurethane membrane 36 covers the enzyme layers and electrodes. Each of anodes 22 and 32 are connected to a common anode wire 33 that leads out of the sensor for electrical connection to an electrometer. Similarly each of cathodes 24 and 34 are connected to a common cathode lead 38, which leads out of sensor 18 for electrical connection to the electrometer.

Figure 3:
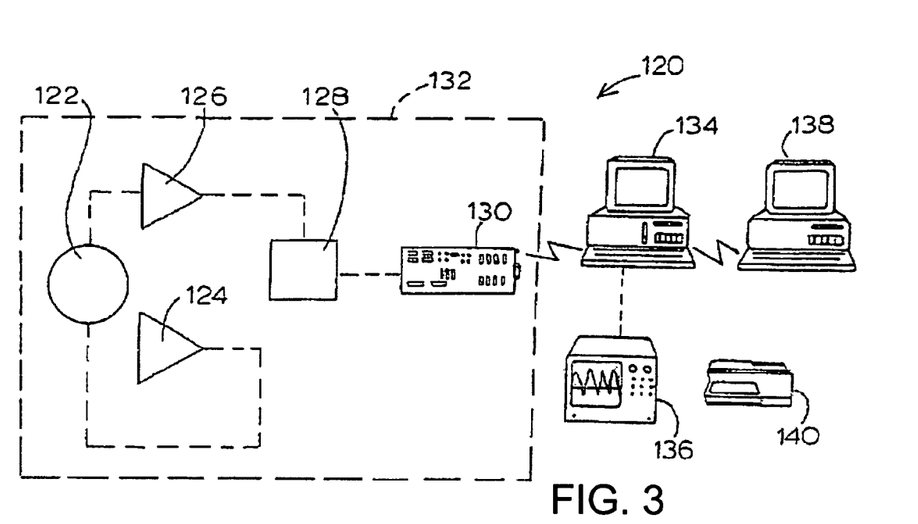
FIG. 3 is a schematic flow chart of an analyte monitoring system, including an analyte sensor, electronics, telemetry, and computing components.

FIG. 3 shows schematically how an implantable analyte sensor (in this embodiment, a glucose sensor) may be connected in a glucose monitoring system 120. Electrodes in sensor 122 are polarized by polarizing circuit 124.

Sensor 122 is connected to electrometer 126, which is configured to sense small changes in electric current, and to translate electric current measurements into voltage signals. Voltage signals from electrometer 126 are telemetry conditioned at 128, and conveyed to a transmitter 130 for radio transmission. All of the components within box 132 may be implanted into the patient as a single unit.

Externally, radio signals from transmitter 130, which in this embodiment are indicative of glucose concentrations in the patient's blood, are transmitted to a receiver 134. Receiver 134 may be connected to a monitor 136 for data monitoring. The same receiver computer, or another computer 138, may be used to analyze the raw data and to generate glucose concentration information. A printer 140 may be connected to computer 138 and configured to generate hard copies of the analyzed data.

Figure 3A:
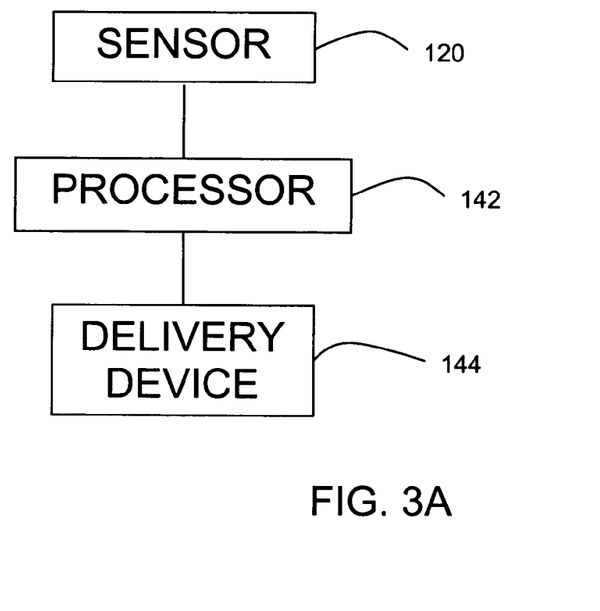
FIG. 3A is a schematic drawing of a system for sensing analyte levels and delivering an appropriate amount of a modulating substance.

FIG. 3A shows a flow chart illustrating a system for correcting analyte concentrations in a mammal. Sensor 120 is a sensor configured to detect electrochemical characteristics in a bodily fluid such as blood, indicative of analyte concentration. For example, sensor 120 may use an enzyme such as glucose oxidase to detect changes in glucose concentration. Alternatively, sensor 120 may use enzymes such as cholesterol oxidase or other enzymes to detect concentrations of other analytes.

Sensor 120 transmits data to processor 142. Processor 142 uses a fading memory algorithm to calculate an appropriate response such as an amount of insulin to deliver for normalizing an abnormal glucose concentration.

Processor 42 communicates instructions to delivery device 144 resulting in delivery of the corrective substance to the patient. Any one, two, or all of the components including sensor 120, processor 142, and delivery device 144 may be positioned inside or outside the patient.

II. FMPD ALGORITHMS

This section describes a novel algorithm that may be used to analyze data indicative of analyte concentration—such as data obtained with the sensor system described in Section I above—and to determine a response. Typically, the response will take the form of a fluid infused into the patient's blood, into the subcutaneous tissue or ino the peritoneal space, to compensate for any surplus or deficiency in the measured analyte concentration. In this section, the following additional abbreviations and definitions will be used:

PE=proportional error=the difference between a measured analyte value and a desired analyte value DE=derivative error=deviation of the rate of change of an analyte value from zero $K_{PE}$=gain coefficient for proportional error $K_{DE}$=gain coefficient for derivative error $W_{PE}$=weight given to a proportional error $W_{DE}$=weight given to a derivative error $P_{DE}'$=weighted proportional error term that includes the gain coefficient factor (see equation 2 below)

DE'=weighted derivative error term that includes the gain coefficient factor (see equation 3 below)

$Z_{PE}$=historical steepness coefficient for proportional error.

$Z_{DE}$=historical steepness coefficient for derivative error t=time, measured backward from the present (i.e., t=10 indicates 10 minutes back into history R=analyte infusion rate In terms of these definitions, the fundamental equation utilized by the FMPD algorithm is:

$$R = \frac{1}{n}\sum_{i=1}^{n} \{PE'(t_i) + DE'(t_i)\} \quad (1)$$

where each sum is over any desired number n of discrete analyte measurements (also known as history segments), and where the terms in each sum are defined at each particular time $t_i$ by:

$$PE'(t_i) = K_{PE} \times W_{PE}(t_i) \times PE(t_i) \quad (2),$$

$$DE'(t_i) = K_{DE} \times W_{DE}(t_i) \times DE(t_i) \quad (3).$$

The weight factors $W_{PE}$ and $W_{DE}$ in equations (2) and (3) generally may be any factors that decrease with increasing time (measured backward from the present), so that contributions to the sum in equation (1) are weighted less heavily at more remote times. In one embodiment, these factors are defined as decaying exponential functions:

$$W_{PE}(t) = e^{-Z_{PE}t} \quad (4),$$

$$W_{DE}(t) = e^{-Z_{DE}t} \quad (5).$$

The normalizing factor 1/n is provided in equation (1) to compensate for the fact that making the measurement interval smaller (say, every one minute instead of every 5 or 10 minutes) will increase the number of terms, and thus make the sum of the weighted terms in equation (1) larger. However, in an alternate embodiment, this factor may equivalently be incorporated into any of the elements appearing in equations (2) or (3), so that its appearance in equation (1) is somewhat arbitrary.

In the embodiment represented by equations (4) and (5), the values of the steepness coefficients $Z_{PE}$ and $Z_{DE}$ determine the rate of exponential decay of the weight factors, and thus, along with the values of the gain coefficients $K_{PE}$ and $K_{DE}$, determine the relative weights of the various terms in the sum of equation (1). Thus, by varying the magnitudes of $Z_{PE}$ and $Z_{DE}$, one can vary the degree to which the history of analyte values—in the form of the proportional error and the derivative error—are utilized. More specifically, smaller values of $Z_{PE}$ and $Z_{DE}$ result in a more slowly decaying weight function, so that the past history of the analyte's behavior being taken into greater consideration, whereas larger values of $Z_{PE}$ and $Z_{DE}$ result in a more rapidly decaying weight function, so that the past history is given less weight.

The values of the steepness coefficients $Z_{PE}$ and $Z_{DE}$ relative to each other also may be adjusted to change the relative importance of the history of the proportional error versus the history of the derivative error. For example, if $Z_{DE}$ is chosen to be larger than $Z_{PE}$, the derivative error weight will decay more rapidly than the proportional error weight, so that less of the history of the derivative error will be taken into account in comparison to the history of the proportional error. Conversely, by choosing $Z_{PE}$ larger than the $Z_{DE}$, less of the history of the proportional error will be taken into account in comparison to the history of the derivative error.

Other embodiments of an FMPD algorithm may display similar, but non-exponential behavior. For example, the weights of the terms in equation (1) may decrease linearly or polynomically backward in time, rather than exponentially. Generally, FMPD algorithms are characterized by the time-dependent weight of the terms that determine the rate of fluid infusion—with more remote terms being weighed less heavily than more recent terms—rather than by the precise functional dependence of those terms on time.

The values of the gain coefficients $K_{PE}$ and $K_{DE}$ affect the overall weight of the proportional error relative to the weight of the derivative error, irrespective of the values of the steepness coefficients $Z_{PE}$ and $Z_{DE}$. Thus, a large value of $K_{PE}$ relative to the value of $K_{DE}$ leads to a greater weighting of all of the proportional errors compared to the derivative errors, independent of the manner in which the weights of the various errors change over time.

III. EXAMPLES

This section describes several examples of systems using analyte sensor systems and/or FMPD algorithms such as those described in Sections I and II above.

Example 1

Animal Trials

This example describes the use of an FMPD algorithm in a trial involving laboratory rodents. Using Labview 6.1 software (National Instruments Inc, Austin Tex.), a software package was developed that implemented the FMPD algorithm. In the developed package, the main parameters of the algorithm are adjustable by the user. Measured glucose levels are entered into the program manually to compute the prescribed insulin dose. The program also contained a feature for running simulations based on data entered in a text file. In one embodiment of the FMPD algorithm, the values of the coefficients of the algorithm were set as follows:

$K_{PE}$=0.00015
$K_{DE}$=0.025
$Z_{PE}$=0.025
$Z_{DE}$=5

In order to create a model of Type 1 diabetes, Sprague-Dawley rats (Charles River Labs, Charles River, Mass., 01887) weighing 300-500 grams were given 200 mg/kg of alloxan. Only animals whose subsequent blood ketone values were greater than 1.5 mM (i.e. those considered to have Type 1 diabetes) were included in the study. Animals were treated every day with one or two subcutaneous injections of Lantus (Insulin Glargine, Aventis, Bridgewater, N.J., 08807) and/or Regular insulin (Novo-Nordisk, Copenhagen).

Rats underwent closed loop studies for six hours while on a homeothermic blanket (Harvard Apparatus, Holliston, Mass.) under anesthesia (1.5-2.5% isoflurane with 40% oxygen and 1 L/min medical air). Venous access was created by placing a 26 g catheter in the saphenous vein. The tip of the animal's tail was nicked to measure blood glucose concentration every five minutes throughout the study. Measurements were made with two hand held glucose meters (Sure Step, Johnson & Johnson Lifescan, Milipitas, Calif., 95035; AccuChek, Roche Diagnostics, Indianapolis, Ind., 46038), the mean value of which was used to calculate the insulin infusion rate. A thirty minute baseline preceded initiation of the FMPD algorithm-based insulin infusion. The insulin was diluted, one unit of Regular insulin (Novo, Copenhagen) per one ml saline. The diluted insulin was placed in a syringe pump (PHD 2000, Harvard Apparatus, Holliston, Mass.) and infused into the saphenous vein catheter. The mean of the blood glucose at each five minute reading was entered into the FMPD algorithm. Insulin infusion rates calculated by the FMPD were followed for the final five-and-a-half hours of the study.

Figure 4:
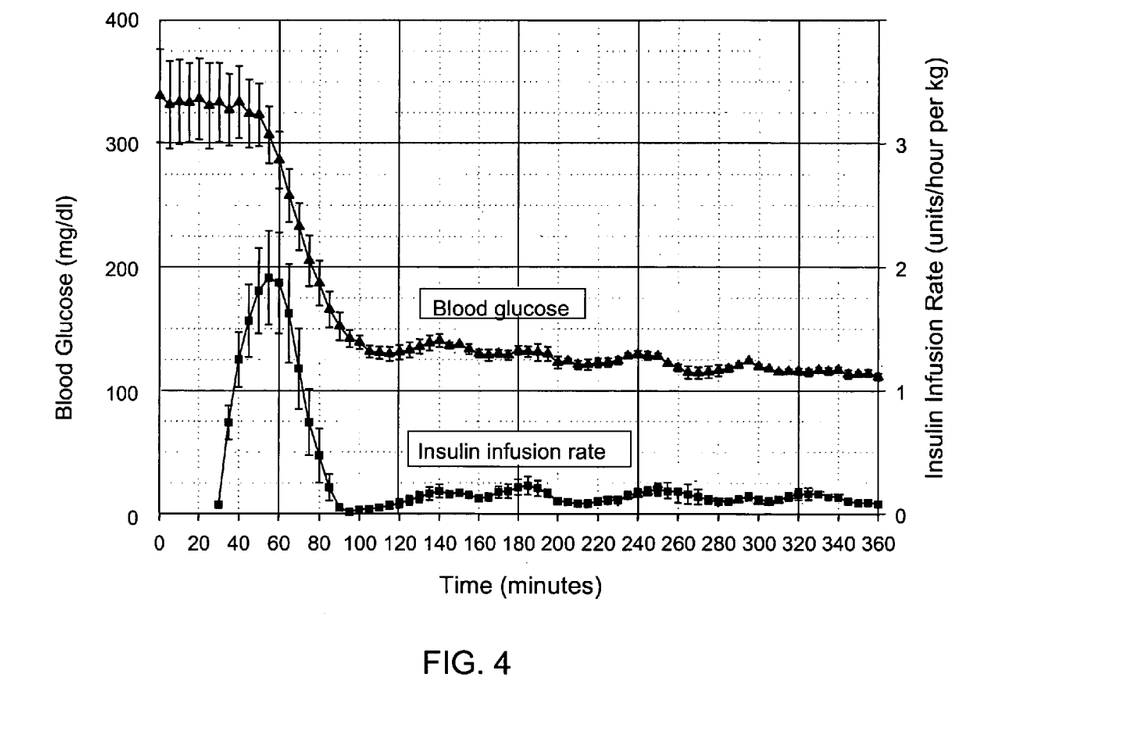
FIG. 4 is a graph illustrating results of a closed loop insulin infusion experiment in rats.
Figure 5:
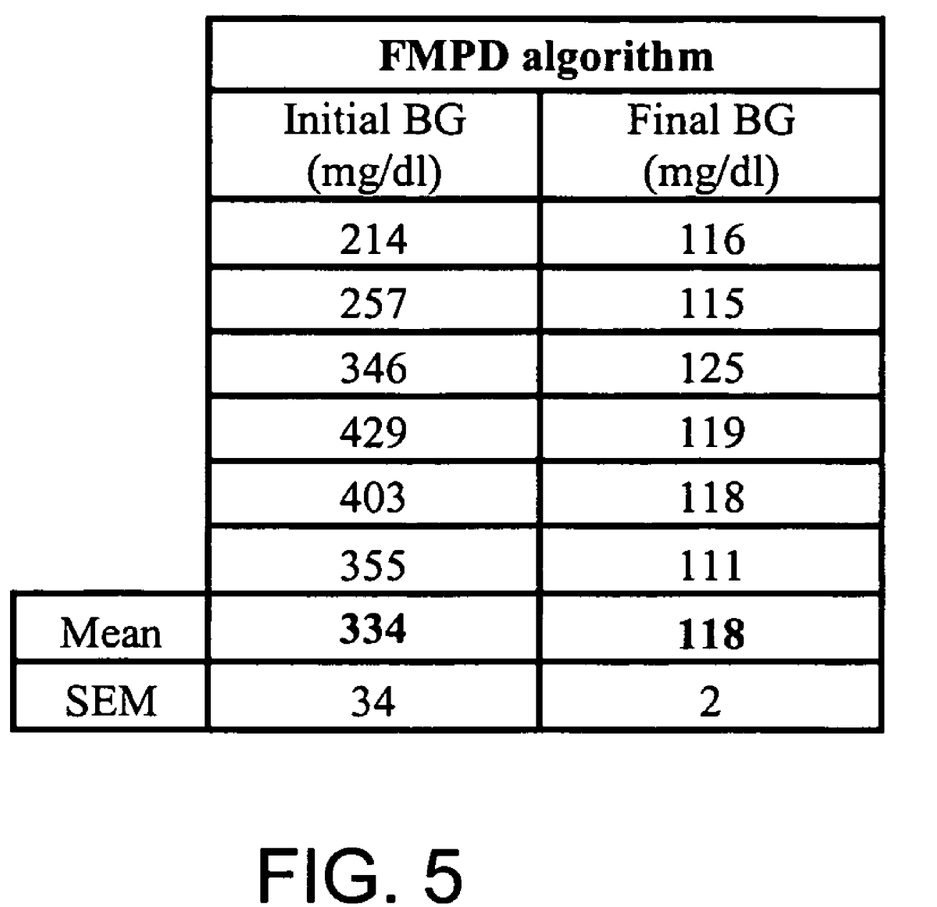
FIG. 5 is a table comparing glucose levels in rats before and after insulin infusion.

In addition to steady state assessments, dynamic aspects of closed loop control were also examined. These aspects included the oscillations of glucose level during the final 240 minutes of the closed loop control study. After identification of peaks and valleys, we then calculated the frequencies of oscillations in all studies and examined the degree to which the oscillations were convergent (decreasing amplitudes over time) or divergent (increasing amplitudes). During closed loop control, in an ideal situation, oscillations of glucose should be of small amplitude and should not increase over time. Students' unpaired t tests were used for comparisons, and data are presented as mean+SEM. A level of 0.05 was used as the criterion for significance. Results of closed loop studies are shown in FIG. 4, which portrays mean (+standard error of the mean) data for blood glucose measurements and insulin infusion rates for 6 diabetic rats. The FMPD algorithm was used to control blood glucose in these animals. A low rate basal insulin infusion was given such that insulin infusion persisted even when glucose was slightly lower than the setpoint of 100 mg/dl. See also FIG. 5, which shows that the final glucose level was much lower than the initial glucose level in all animals. The final glucose level averaged 118+2.0 mg/dl (minutes 240-360).

Figure 6:
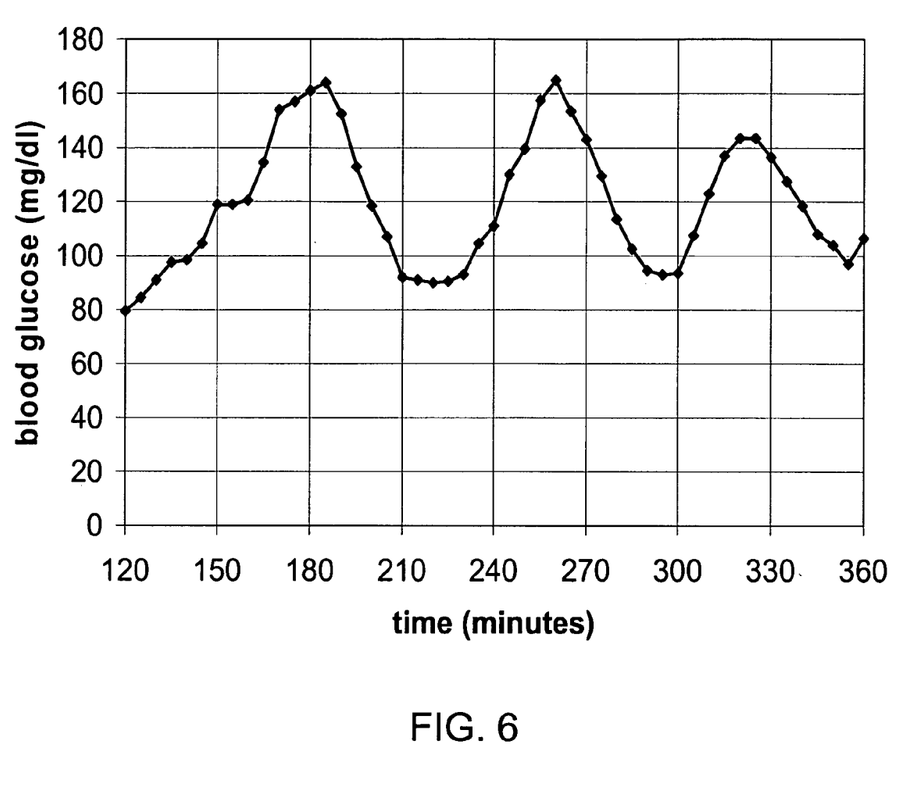
FIG. 6 shows a graph plotting glucose oscillations versus time in a single animal.

The amplitude of oscillations (distance from peak to valley) averaged 10.7+2.9%. In terms of assessing whether oscillations converged or diverged over the course of the final 4 hours of the study, we compared amplitude data during early control in minutes 120-235 with later control in minutes 240-360. An example in one animal of the oscillations during the final four hours of the study is shown in FIG. 6. There was a tendency for glucose values to converge, rather than to diverge during closed loop control. The oscillation frequency averaged 0.79 cycles per hour.

By analysis if the foregoing results, it can be understood that the FMPD algorithm is a novel closed loop insulin control algorithm that utilizes a time-related weighting of proportional and derivative glucose data. The weighting function can be thought of as a fading memory of glucose levels and trends, and is based on the fact that the islet's physiological response to glucose utilizes current information and a fading memory of previous information. Animal studies showed that blood glucose was very well controlled during the closed loop control studies. This comparison demonstrates that, in the setting of venous glucose sampling and venous insulin delivery, this method enhances glucose control without causing undue hypoglycemia. In the situation in which there is a greater efferent delay or greater afferent delay, a less aggressive approach (using lower gain parameters) may be necessary to minimize the risk of hypoglycemia.

Example 2

Gain Scheduling

One of the potential problems with a closed loop system of glucose control is that there can be a delay of the action of the infused insulin. For example, if one gives insulin by subcutaneous infusion, its action is much slower (due to the need for insulin to be absorbed before its action can be exerted) than if one gives the insulin intravenously. When a delay exists, it raises the possibility of overcorrection hypoglycemia. For example, assume that glucose is rising and that accordingly, the calculated insulin infusion rate also rises. However, let us assume that there is also a delay in the action of insulin in terms of its effect to reduce glucose level. The potential problem is that the algorithm will continue to increase the insulin infusion rate and that by the time the insulin finally acts, there will be a great deal of insulin that has been administered. Accordingly, the glucose can fall to very low values, a problem termed overcorrection hypoglycemia.

One method of reducing the chance of experiencing overcorrection hypoglycemia is to rapidly reduce (or discontinue) the insulin infusion rate as soon as glucose begins to fall (or even as soon as the rate of rise of glucose declines towards zero). Such adjustments can be termed gain scheduling, that is making an adjustment during the algorithm utilization based on results obtained during closed loop control.

Gain scheduling is a method that can be included in many types of algorithms. Gain scheduling essentially adjusts the gain parameters of the control algorithm such that desired responses can be obtained according to different ongoing results. Gain parameters are adjusted based on decision rules that utilize functions of input and output parameters. When considering the extremes of blood glucose levels, hypoglycemia is acutely more serious than hyperglycemia. If hypoglycemia is severe enough, coma, seizures or death may occur. The effects of hyperglycemia on the body are inherently slower and less of a problem from an acute (immediate) stand point. For these reasons, a quicker response to falling glucose in comparison to rising glucose may be desirable. Such a quick response may be accomplished by gain scheduling so that the response to rising and falling glucose levels are different. There are many possible methods of employing such gain scheduling. One such method defines zones using inverse polynomial curve fitting, as shown in FIG. 7.

Figure 7:
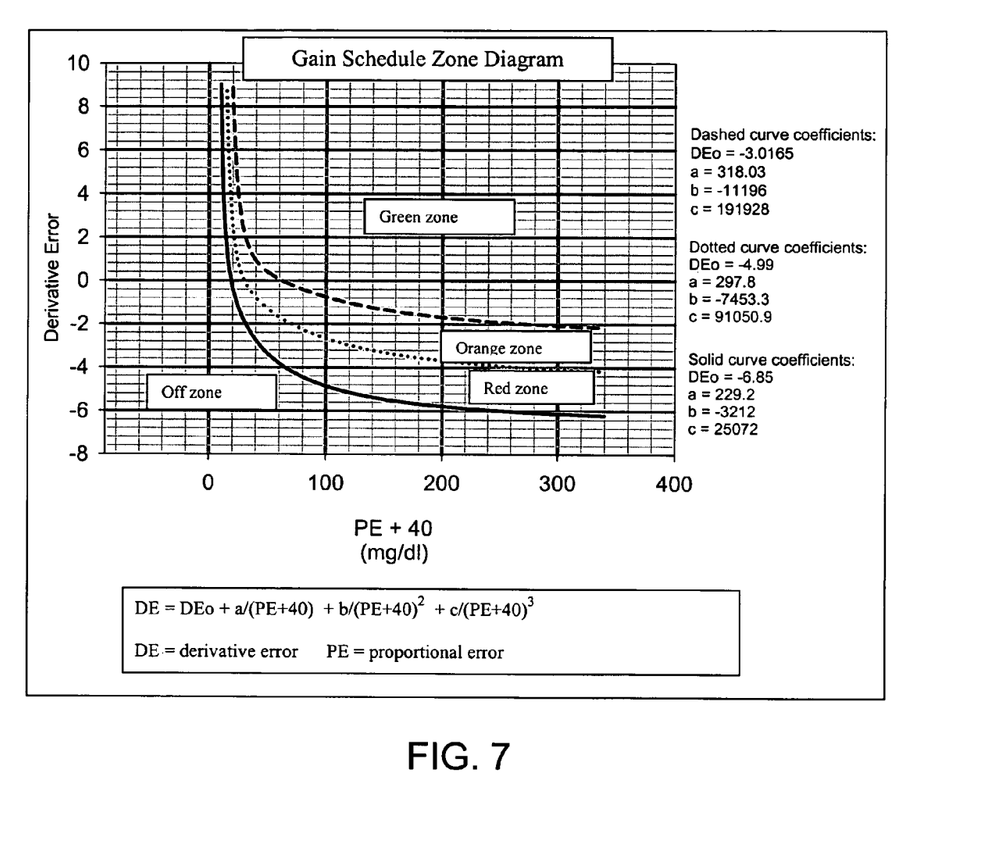
FIG. 7 is a graph showing a gain schedule zone diagram.

In FIG. 7, each zone indicates the need for a specific action by the algorithm. For example, let us assume that the current glucose concentration is 160 mg/dl. If the goal is 100 mg/dl, then the PE=60 mg/dl (and the X axis, PE+40, is 100 mg/dl). If the glucose concentration is rising and the specific DE is 2, then the data pair falls into the green zone. Data within the green zone indicates that the computed insulin infusion rate (R) will not be altered (since there is a very low risk for hypoglycemia). If on the other hand, the PE remains at 60 (PE+40=100) and the DE is equal to −2, the data fair falls into the orange zone, indicating that there is a risk for hypoglycemia. Data pairs in the orange zone indicate that the $Z_{PE}$ coefficient must be multiplied by a factor (chosen in one embodiment to be 2), thereby reducing the historical contribution, which in turn reduces the sum of the PE' terms, which then reduces the overall infusion rate R.

Another illustrative example of gain scheduling is one in which PE remains unchanged and DE is −4. This would be the case, for example, if glucose concentration were falling rapidly. The data pair in this case falls into the red zone. Data pairs in the red zone indicate that the $Z_{PE}$ coefficient is multiplied by a greater factor (chosen in one embodiment to be 4), further reducing the historical contribution, and thus further reducing the overall infusion rate R. In the situation in which PE remains unchanged and DE is −6, the data pair falls into the Off zone, which means that the infusion rate R is immediately turned off.

Use of the zone diagram illustrated in FIG. 7, which utilizes gain scheduling, is a cautionary measure to respond quickly to declining glucose values during closed loop control in order to reduce the risk for hypoglycemia. Persons skilled in the art will understand that other, similar methods of gain scheduling can be utilized with an FMPD algorithm.

For the algorithm as described above, if the glucose level remains at the goal, there is no proportional and no derivative error, and therefore no insulin will be infused. Let us assume that the goal is set at 100 mg/dl. It is known that the normal pancreatic islet cells continue to secrete insulin even thought glucose concentration may be equal or below 80 mg/dl. So, if the glucose goal is set at a level above the normal set point of the pancreatic islet cells, a basal insulin infusion rate may be added to the algorithm. If the goal is set a lower value and is similar to the true pancreatic set point, a separate basal insulin infusion will not be needed.

Example 3

Comparison to Other Algorithms

The use of proportional error (PE) and derivative error (DE) terms as used in glucose control has been discussed by others for use in an artificial pancreas, and algorithms incorporating these two errors have been termed proportional derivative (PD) algorithms. For example, a glucose-controlled insulin infusion system incorporating a PD method is disclosed in U.S. Pat. No. 4,151,845 to Clemens.

Glucose history may be incorporated into an algorithm for determining a response by using a Proportional, Integral, Derivative (PID) method, which incorporates an integral term into the algorithm. Steil, et al. disclosed the use of a PID algorithm in an artificial pancreas in U.S. Pat. No. 6,558,351. The PID algorithm can be summarized as follows. Assume that in the situation of serial glucose measurements, one plots the proportional error (current glucose concentration minus the glucose goal) on the ordinate and the time over which the measurements were made on the abscissa. The area under the curve from time x to time y is the integral, and this term provides some information about the history of the glucose values.

The FMPD algorithm of the present disclosure does not incorporate an integral term in the algorithm, and can be distinguished from PID algorithms quite readily. In FMPD algorithms, a time-weighting method is used for the analyte proportional error and the analyte derivative error. For both the proportional error and the derivative error, analyte values that are more recent are weighted more heavily than more remote values, and the degree to which more recent values are weighted more heavily than more remote values can be varied. In other words, the algorithm can be made to increase its response to prior events (but never so much that it responds to remote data more than more recent data).

In the specific context of an artificial pancreas, the FMPD algorithms of the present disclosure also can be compared to a PID algorithm in terms of how each reflects the normal physiology of pancreatic islet function. In terms of designing a closed loop artificial pancreas algorithm, it should be emphasized that the normal islet response to glucose comes to a plateau over time despite the presence of continued steady hyperglycemia. For example, in perifused islets and in non-diabetic humans who undergo hyperglycemic glucose clamps, insulin secretion typically begins to plateau within a two hour period despite a continued elevation of glucose. The time-related decrease in response is somewhat dependent on the degree of hyperglycemia; there may be less of a plateau with marked hyperglycemia. At any rate, after many hours, there is little or no continued rise in insulin secretion despite the persistence of hyperglycemia.

In an artificial pancreas system based on a PID algorithm, the integral factor responds to the duration of glucose elevation in a linear manner. That is, the magnitude of the insulin delivery rate is directly proportional to the length of time that the glucose concentration remains elevated. In a PID system, if glucose remains elevated at a constant level, the integral component will continue to rise in a linear fashion, rather than reach a plateau.

Figure 8:
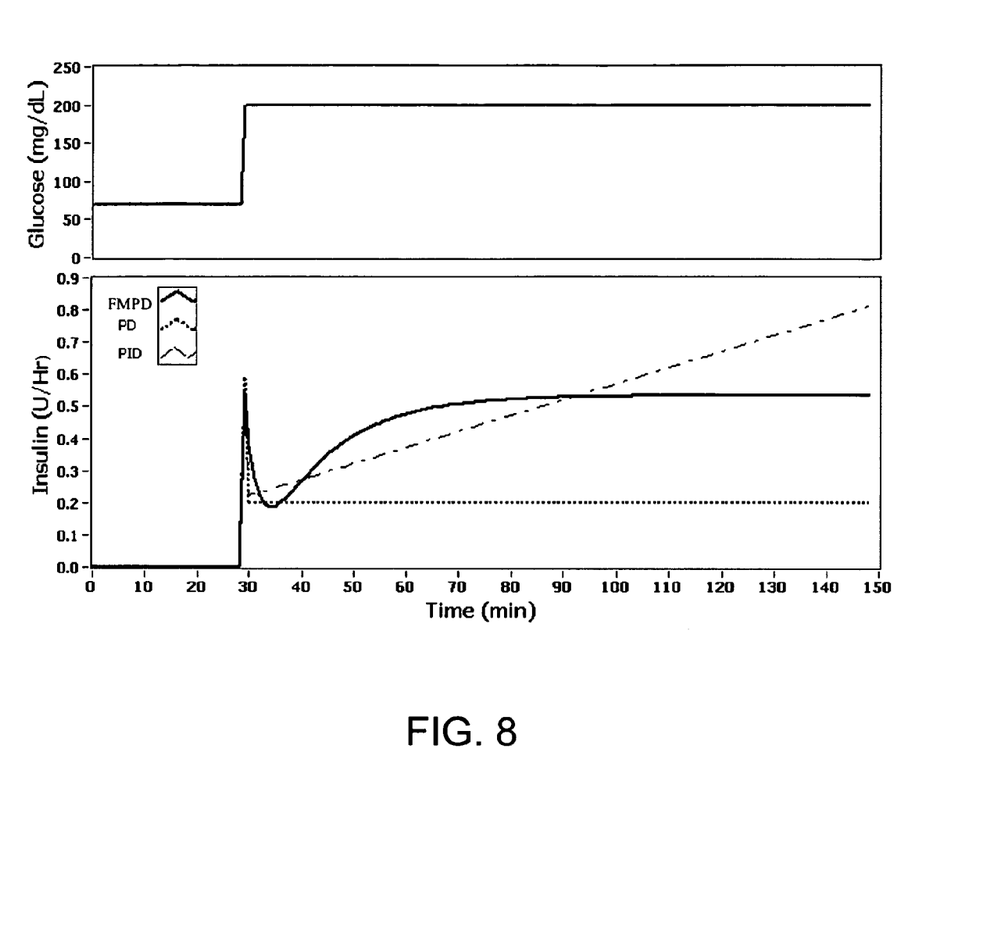
FIG. 8 is a graph showing pancreatic response profiles using three different algorithms.

To compare the pancreatic response modeled by proportional derivative without fading memory (PD), PID without fading memory, and FMPD algorithms, we performed computations which simulated a hyperglycemic glucose clamp. The glucose values at every minute of the clamp profile were submitted to three algorithms: PD, PID and FMPD. The resulting insulin responses are shown in FIG. 8, which demonstrates that, like the normal physiologic response, all three algorithms demonstrate a biphasic response to elevated glucose. For both the PD and the PID algorithms, the first phase exists only at the instant when glucose level changed.

More specifically, the FMPD algorithm produces a first phase response that persists even after the instantaneous glucose rise. For the PD algorithm, the second phase insulin release is constant (unlike the normal situation, it does not rise). The PID algorithm produces a more realistic second phase in which the insulin infusion rate rises; however, the PID second phase continuously ramps up for the duration of the elevation of glucose concentration. This is because the integral action continues to add to the total insulin dose for as long as the glucose is above the set-point. The fading memory algorithm also produces an increasing second phase, but it reaches a plateau after a period of time, depending on the magnitude of the $W_{PE}$ parameter. The FMPD algorithm in the present invention simulates the physiological situation of reaching a plateau by applying a fading memory of glucose data to the proportional and derivative components. The invention is based on the fact that the islet's physiological response to glucose is based on current information in addition to a fading memory of previous information.

Example 4

Avoiding Overcorrection Hypoglycemia

In another variation of the described methods, glucagon, or another substance capable of increasing glucose levels, is administered as glucose levels fall to avoid or attenuate hypoglycemia. As described above, insulin is delivered (intravenously, subcutaneously or intraperitoneally) based on the proportional error, the derivative error, as modified based on history (past proportional and derivative error calculations), which we refer to as "fading memory".

In some instances if the glucose level starts out high, a relatively large dose of insulin is administered based on the algorithm. This may cause an overcorrection resulting in hypoglycemia several hours after giving the high dose of subcutaneous insulin. It is generally not practical or effective merely to turn off the insulin to avoid overcorrection hypoglycemia because subcutaneous insulin has a long delay before it is absorbed and its effect may last for hours after it is given.

Overcorrection hypoglycemia is typically not a problem when insulin is administered intravenously because its onset and offset is relatively rapid. However, when insulin is administered subcutaneously resulting in a rapid decline in glucose concentration, glucagon, or some other agent capable of increasing blood glucose levels (glucagon-like agent), or small volumes of concentrated glucose itself (for example 15-50% dextrose) may be adminstered subcutaneously.

Glucagon is an endogenous hormone that all mammals secrete from the pancreas. Glucagon is a linear peptide of 29 amino acids. Its primary sequence is almost perfectly conserved among vertebrates, and it is structurally related to the secretin family of peptide hormones. Glucagon is synthesized as proglucagon and proteolytically processed to yield glucagon within alpha cells of the pancreatic islets. Proglucagon is also expressed within the intestinal tract, where it is processed not into glucagon, but to a family of glucagon-like peptides (enteroglucagon).

In contrast to insulin, subcutaneous glucagon has a faster onset and offset. Studies have shown glucagon onset five to ten minutes after subcutaneous delivery, whereas insulin onset may take hours after subcutaneous delivery. Therefore it can be used effectively as a "rescue treatment" when the glucose level is declining rapidly. This has proven beneficial in animal studies to minimize overcorrection hypoglycemia.

For example, to avoid overcorrection hypoglycemia, glucagon, a glucagon-like agent, or some form of glucose itself, may be administered when blood glucose concentration is 100 mg/dl and falling rapidly. The calculation for dosing glucagon in a closed loop system is similar to that of insulin, except in reverse. The amount of glucagon given should be based on the proportional error. Assume a set point of 100 mg/dl, more glucagon is delivered if the glucose level is 60 than if the glucose level is 90. The amount of glucagon delivered should also be based on the derivative error (again the goal of the derivative error is 0—flat). In other words, if glucose is declining at 6 mg/dl per min, then one should give more glucagon than if it is declining at 1 mg/dl per minute.

The fading memory factor is less important relative to the derivative error for glucagon administration, but is more useful relative to the proportional error. Therefore, preferably, a fading memory calculation is used, as described with respect to insulin delivery, for administering glucagon, mainly with respect to the proportional error, while considering none or only a short history relative to the derivative error. In other words, it will typically be useful to consider a longer history for the proportional error than for the derivative error.

For example, assume patient A has had a glucose concentration slope of 1 for at least forty five minutes, and currently has a glucose concentration of 80 mg/dl; patient B has had a glucose concentration slope of 1 for only a short period, and currently has a glucose concentration of 80. Patient A has a higher risk of hypoglycemia than patient B, but perhaps not a lot higher. Both patients have a glucose concentration falling at the same rate, and both patients are nearing hypoglycemia. However, if the glucose level (proportional error) is unchanged compared to thirty minutes ago when glucagon was administered, then more glucagon should be administered immediately.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of determining a fluid infusion rate for infusing a fluid containing insulin into a user, comprising
    using a glucose detection device to monitor concentration of glucose in the user and generating a sensor output signal based on the monitored concentration,
    using the sensor output signal to generate a processor input signal,
    processing the processor input signal using a fading memory proportional derivative algorithm to generate a processor output signal,
    determining a fluid infusion rate based at least partially on the processor output signal wherein the fluid contains insulin,
    delivering the fluid containing insulin into the user, and
    delivering a glucose-increasing substance to the user when the user's glucose concentration is falling at a rate above a pre-determined threshold, and the user's glucose concentration has fallen below a pre-determined threshold level.

2. The method of claim 1, wherein the glucose-increasing substance is selected from the following: (a) glucagon, (b) glucagon-like agent, (c) glucose, and (d) dextrose, and mixtures thereof.

3. The method of claim 1, further comprising receiving the sensor output signal at a transmitter electrically coupled to the sensor, converting the sensor output signal to the processor input signal with the transmitter, and transmitting the processor input signal to the processor with the transmitter.

4. The method of claim 1, wherein determining the fluid infusion rate also is based on at least one of the following traits of the user: insulin sensitivity, age, body weight, usual total daily insulin dose, or physical adiposity.

5. The method of claim 1 further comprising implanting the glucose detection device in the user.

6. A method of determining a fluid infusion rate for infusing a fluid containing insulin into a user, comprising
    using a glucose detection device to monitor concentration of glucose in the user and generating a sensor output signal based on the monitored concentration,
    using the sensor output signal to generate a processor input signal,
    processing the processor input signal using a fading memory proportional derivative algorithm to generate a processor output signal,
    determining the fluid infusion rate based at least partially on the processor output signal,
    delivering the fluid containing insulin into the user, and
    delivering a glucose-increasing substance to the user when the user's glucose concentration is falling, the timing and amount of glucose-increasing substance delivered being based on a proportional error of glucose concentration and a derivative error of glucose concentration.

7. The method of claim 6, wherein the timing and amount of glucose-increasing substance delivered is based at least partially on a fading memory calculation relative to the proportional error.

8. The method of claim 6, wherein the timing and amount of the glucose-increasing substance delivered is based at least partially on a fading memory calculation relative to the derivative error.

9. The method of claim 6, wherein the timing and amount of the glucose-increasing substance delivered is based at least partially on fading memory calculations relative to the proportional error and the derivative error, a longer history being considered relative to the proportional error compared to the history considered for the derivative error.

* * * * *